US008642255B2

(12) United States Patent
Nicoud et al.

(10) Patent No.: US 8,642,255 B2
(45) Date of Patent: Feb. 4, 2014

(54) MATERIALS AND METHODS FOR HYPOTHERMIC COLLECTION OF WHOLE BLOOD (75) Inventors: Ian B. Nicoud, Seattle, WA (US); Dominic M. Clarke, Bothell, WA (US); Aby J. Mathew, Vestal, NY (US); Michael Rice, Woodinville, WA (US)

(73) Assignee: Biolife Solutions, Inc., Bothell, WA (US)

( * ) Notice: Subject to any disclaimer, the term of this patent is extended or adjusted under 35 U.S.C. 154(b) by 235 days.

(21) Appl. No.: 12/934,644

(22) PCT Filed: Mar. 27, 2009

(86) PCT No.: PCT/US2009/038634
§ 371 (c)(1),
(2), (4) Date: Mar. 8, 2011

(87) PCT Pub. No.: WO2009/121002
PCT Pub. Date: Oct. 1, 2009

(65) Prior Publication Data
US 2011/0152719 A1 Jun. 23, 2011

Related U.S. Application Data (60) Provisional application No. 61/039,966, filed on Mar. 27, 2008, provisional application No. 61/039,978, filed on Mar. 27, 2008.

(51) Int. Cl.
A01N 1/02 (2006.01)
(52) U.S. Cl.
USPC .......................................................... 435/2
(58) Field of Classification Search
None
See application file for complete search history.

(56) References Cited

U.S. PATENT DOCUMENTS

| | | | |
|---|---|---|---|
| 4,112,070 A | 9/1978 | Harmening | |
| 4,386,069 A * | 5/1983 | Estep | 424/533 |
| 4,838,861 A | 6/1989 | Sharp | |
| 4,880,786 A | 11/1989 | Sasakawa et al. | |
| 5,004,681 A | 4/1991 | Boyse et al. | |
| 5,053,025 A | 10/1991 | Knippscheer | |
| 5,059,168 A | 10/1991 | Stone | |
| 5,114,672 A | 5/1992 | Knippscheer et al. | |
| 5,192,553 A | 3/1993 | Boyse et al. | |
| 5,372,581 A | 12/1994 | Anderson | |
| 5,415,665 A | 5/1995 | Hessel et al. | |
| 5,919,176 A | 7/1999 | Kuypers et al. | |
| 5,993,429 A | 11/1999 | Kuypers et al. | |
| 6,045,990 A | 4/2000 | Baust et al. | |
| 6,102,871 A | 8/2000 | Coe | |
| 6,238,907 B1 | 5/2001 | Schuler-Maloney | |
| 6,280,724 B1 | 8/2001 | Moore | |
| 6,302,854 B1 | 10/2001 | Paderni | |
| 6,492,103 B1 | 12/2002 | Taylor | |
| 6,994,954 B2 | 2/2006 | Taylor | |
| 7,083,587 B2 | 8/2006 | Chattopadhyay et al. | |
| 7,112,576 B1 | 9/2006 | Hubel | |
| 7,112,653 B2 | 9/2006 | Moore | |
| 7,147,626 B2 | 12/2006 | Goodman et al. | |
| 7,211,191 B2 | 5/2007 | Coelho et | |
| 7,255,879 B2 | 8/2007 | Hariri | |
| 7,294,144 B1 | 11/2007 | Schneider | |
| 2002/0123141 A1 | 9/2002 | Hariri | |
| 2003/0113911 A1 | 6/2003 | Scholl et al. | |
| 2005/0084838 A1 | 4/2005 | Lampeter | |
| 2005/0233298 A1 | 10/2005 | Farsedakis | |
| 2007/0048726 A1 | 3/2007 | Baust et al. | |
| 2009/0123436 A1 * | 5/2009 | Opperman | 424/93.7 |

FOREIGN PATENT DOCUMENTS

| | | |
|---|---|---|
| WO | 91/09521 | 7/1991 |
| WO | 92/03180 | 3/1992 |
| WO | 00/02572 | 1/2000 |
| WO | 03043419 A1 | 5/2003 |
| WO | 03043571 A2 | 5/2003 |
| WO | 2005042060 A2 | 5/2005 |
| WO | 2009/121002 | 10/2009 |

OTHER PUBLICATIONS

Buetler et al., Blood, vol. 54, 1979, pp. 280-284.*
Bhattacharya et al., Journal of American College of Surgeons, vol. 200, No. 4, Apr. 2005, pp. 557-563.*
Biolife Solutions press release, 2007, retrieved from the internet, pp. 1-2.*
Avatar Corporation press release, 2008, retrieved from the internet, pp. 1-2.*
Baust, "Advances in Media for Cryopreservation and Hypothermic Storage," Bioprocess International, Jun. 2005, pp. 2-8.
Hess, "Red cell freezing and its impact on the supply chain," Transfusion Medicine, vol. 14, No. 1, Feb. 2004, pp. 1-8.
Mudge et al., "Comparison of 4 blood storage methods in a protocol for equine pre-operative autologous donation," Veterinary Surgery, vol. 33, No. 5, Sep. 2004, pp. 475-486.

(Continued)

Primary Examiner — Allison Ford
Assistant Examiner — Yvonne Pyla
(74) Attorney, Agent, or Firm — K&L Gates LLP (57) ABSTRACT The present invention relates to materials and methods for hypothermic collection of whole blood, and components thereof, which can extend the holding time of blood beyond the current useable limit. Additionally, blood can be drawn directly into a hypothermic preservation solution without the addition of standard anticoagulants. This is enabled by providing sustained cellular viability under hypothermic conditions using a nutrient matrix devoid of animal proteins and containing energy substrates, free-radical scavengers, and impermeants that is ionically balanced for storage of biologic materials at low temperatures to prevent cellular stress-induced apoptosis.

12 Claims, 3 Drawing Sheets (56) References Cited

OTHER PUBLICATIONS

Richardson et al., "Blood storage at 4° C.—factors involved in DNA yield and quality," *Journal of Laboratory and Clinical Medicine*, vol. 147, No. 6, Jun. 1, 2006, pp. 290-294.

Snyder et al., "Biological Packaging for the Global Cell and Tissue Therapy Markets," *Bioprocessing Journal*, May/Jun. 2004, pp. 1-7.

Stylianou et al., "Novel cryoprotectant significantly proves the post-thaw recovery and quality of HSC from CB," *Cytotherapy*, vol. 8, No. 1, Feb. 2006, pp. 57-61.

Van Buskirk et al., "Hypothermic Storage and Cryopreservation—The Issues of Successful Short-term and Long-term preservation of cells and tissues," *Bioprocess International*, vol. 2, No. 10, Nov. 2004, pp. 42-49.

Van der Meer et al., "Overnight storage of whole blood: A comparison of two designs of butane-1, 4-diol cooling plates," *Transfusion*, vol. 47, No. 11, Nov. 2007, pp. 2038-2043.

PCT International Search Report for International Patent Application No. PCT/US2009/038634, mailed Jul. 8, 2009, 5 pgs.

PCT Written Opinion of the International Searching Authority for International Patent Application No. PCT/US2009/038634, mailed Jul. 8, 2009, 6 pgs.

\* cited by examiner

MATERIALS AND METHODS FOR HYPOTHERMIC COLLECTION OF WHOLE BLOOD

REFERENCE TO RELATED APPLICATIONS

This application is a national phase application under 35 U.S.C. 371 of International Application No. PCT/US2009/038634, filed on Mar. 27, 2009, which claims priority to and the benefit of U.S. Provisional Patent Application No. 61/039,978, filed on Mar. 27, 2008, and U.S. Provisional Patent Application No. 61/039,966, filed on Mar. 27, 2008, the entire disclosures of each of which are hereby incorporated by reference herein.

BACKGROUND OF THE INVENTION

Effective blood cell (BC) biopreservation techniques for maintaining viability and function ex vivo represent the foundation of modern blood banking Routine processes such as collection, storage and transportation, which are performed by donor centers and transfusion services, rely on the ability to prevent or delay the detrimental biochemical, biophysical, and morphologic effects of ex vivo BC preservation. The field of BC biopreservation is driven largely by the clinical need for BC products.

Maintaining the quality and safety of clinically used blood products requires effective techniques for the preservation of BC viability and function. Biopreservation-induced BC injury has a significant impact on transfusion efficacy and can be linked to pro-inflammatory and immunomodulatory effects, increased infections, increased length of stay in the hospital, and increased morbidity and mortality.

Improving hypothermic BC storage practices can have an enormous effect on transfusable blood unit availability, safety, and quality; furthermore, extending hypothermic storage times improves blood logistics by decreasing BC losses due to expiration and transportation, and improving autologous and remote blood storage. For the last 25 years, BC biopreservation research has focused on modifications of storage solution composition, blood collection protocols, and devices in effort to lengthen BC hypothermic storage.

Nevertheless, techniques for liquid storage of BCs have remained relatively unchanged since their inception in the 1940s, and progress in improving the quality and function of hypothermically stored BCs ex vivo has been very slow. The current focus of transfusion medicine has shifted from extending storage times to improving the quality of hypothermically stored blood products.

An object of the present invention is to provide improved methods and materials for hypothermic collection and transport of whole blood that both enhance the quality and extend the viability of whole blood, including cord blood, and components isolated therefrom.

SUMMARY OF THE INVENTION

There is a need, met by embodiments of the present invention, for improved quality and extended holding times for whole blood units or components thereof. As disclosed herein, this is accomplished when such biological materials are contacted with and/or contained within an optimal nutrient-rich environment under hypothermic conditions. Furthermore, utilizing such serum-free, protein free solutions as the preferred hypothermic environment creates an optimal circumstance which allows for cryogenic preservation compatibility for cells between transport and cryoprotective solutions, in addition to eliminating xenographic biologic transmission risk.

The present invention is based on the discovery that a hypothermic preservation solution can be used to collect whole blood and isolate cellular components therefrom as set forth herein. Any preservation solution which is formulated to reduce free radical accumulation in cells undergoing hypothermic preservation to help mediate the level of post-storage necrosis and apoptosis, thereby directly decreasing the level of cell death during and following the preservation interval, is suitable for use. Moreover, further benefits are observed when long-term frozen storage of isolated cellular components is performed using a cryopreservation solution formulated to address the molecular-biological aspects of cells during the cryopreservation process thereby directly reducing the level of Cryopreservation-Induced Delayed-Onset Cell Death and improving post-preservation cell viability and function. Through modulating the cellular biochemical response to the preservation process, such a preservation solution can enhance cell viability and functionality while eliminating the need to include serum, proteins or high levels of cytotoxic agents. Based on these discoveries, previously undescribed preparations and manipulations of whole blood, including, for example, cord blood, are now possible which are unexpected and overcome the limitations of conventional preparations and protocols.

In one aspect, the invention is directed to a method of harvesting whole blood, the method comprising: a) providing a volume of whole blood from a donor; and, b) mixing the volume of whole blood, or a portion thereof, with a volume of preservation solution adapted for cellular osmotic balance at hypothermic temperatures, such that the ratio of whole blood to preservation solution is at least about 1:0.1 by volume. In other preferred embodiments, the ratio of whole blood to preservation solution is at least about 1:0.5, 1:1, 1:2, 1:5, or 1:10. Preferably, the mixture of whole blood and preservation solution is maintained at about 2° C. to about 18° C. The preferred preservation solution is HYPOTHERMOSOL® (HTS-FRS, BioLife Solutions, Inc., Bothell, Wash.). In certain preferred embodiments, the method further includes the step of collecting the whole blood in the presence of an anti-coagulant wherein the anticoagulant is not the same as the preservation solution. In a currently preferred method, the whole blood is cord blood.

Preferably, the preservation solution contemplated herein comprises an ingredient selected from the group consisting of: an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; a biological pH buffer effective under physiological hypothermic conditions; and combinations thereof. One preferred method uses a preservation solution further comprising glutathione, a vitamin E derivative, an antioxidant, or combinations thereof.

In another aspect, the invention provides a method for hypothermic storage of whole blood, the method comprising: a) diluting a volume of whole blood in a volume of preservation solution adapted for cellular osmotic balance at hypothermic temperatures, such that the ratio of whole blood to preservation solution is at least about 1:0.1 by volume; and b)

maintaining the whole blood/preservation solution mixture at about 2° C. to about 18° C. The ratio of whole blood to preservation solution can be at least about 1:0.5, 1:1, 1:2, 1:5, or 1:10 and the preservation solution can be HYPOTHERMOSOL®. In certain embodiments, the whole blood is cord blood.

In yet another aspect, the present invention provides a system for isolation of a component from whole blood, the method comprising: a) providing a volume of whole blood from a donor; b) mixing the volume of whole blood, or a portion thereof, with a volume of preservation solution adapted for cellular osmotic balance at hypothermic temperatures, such that the ratio of whole blood to preservation solution is at least about 1:0.1 by volume; and, c) isolating one or more components from the mixture of whole blood and preservation solution. The system can further comprise the step of: maintaining the mixture of whole blood and preservation solution at a temperature of about 2° C. to about 18° C. until the one or more components is isolated. And, the system can further comprise the step of: cryogenically freezing the one or more isolated components. The ratio of whole blood to preservation solution can be at least about 1:0.5, 1:1, 1:2, 1:5, or 1:10. The preservation solution can be HYPOTHERMOSOL®. In a preferred embodiment, the one or more components comprise stem cells, and the whole blood is cord blood.

In yet another aspect, the present invention is directed to a composition comprising a mixture of whole blood and a preservation solution adapted for cellular osmotic balance at hypothermic temperatures, such that the ratio of whole blood to preservation solution is at least about 1:0.1 by volume. The ratio of whole blood to preservation solution can be at least about 1:0.5, 1:1, 1:2, 1:5, or 1:10. And, the preservation solution comprises an ingredient selected from the group consisting of: an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; a biological pH buffer effective under physiological hypothermic conditions; and combinations thereof. In certain embodiments, the preservation solution further comprises glutathione, a vitamin E derivative, an antioxidant, or combinations thereof. In preferred embodiments, the composition is free of an exogenously-introduced anticoagulant reagent. In other embodiments, the composition further comprises an exogenously-introduced anticoagulant agent which is not the same as the preservation solution. In a preferred composition, the whole blood is cord blood.

In yet another aspect, the present invention is directed to a method for harvesting one or more components from whole blood, wherein the whole blood is obtained from an umbilical cord having a first end and a second end. The method can include the steps of clamping the first end of the umbilical cord; clamping the second end of the umbilical cord, thereby trapping a volume of umbilical cord blood within the umbilical cord between the first end and the second end of the umbilical cord; venipuncturing the first end of the umbilical cord; and draining umbilical cord blood into a container containing a first volume of preservation solution adapted for cellular osmotic balance at hypothermic temperatures. The method can include the additional step of flushing the umbilical cord with a second volume of preservation solution adapted for cellular osmotic balance at hypothermic temperatures. The preservation can be HYPOTHERMOSOL®. In some embodiments, the one or more components include stem cells.

In yet another aspect, the present invention is directed to a method for harvesting one or more components from whole blood, wherein the whole blood is obtained from an umbilical cord having a first end and a second end. The method can include the steps of clamping the first end of the umbilical cord; clamping the second end of the umbilical cord, thereby trapping a volume of umbilical cord blood within the umbilical cord between the first end and the second end of the umbilical cord; and unclamping the first end of the umbilical cord to drain the umbilical cord blood into a container containing a volume of preservation solution adapted for cellular osmotic balance at hypothermic temperatures. The preservation solution can be HYPOTHERMOSOL®. In some embodiments, the one or more components include stem cells.

In a further aspect, the present invention is directed to a method of harvesting whole blood. The method can include the steps of providing a volume of whole blood from a donor; and mixing the volume of whole blood, or a portion thereof, with a volume of preservation solution adapted for cellular osmotic balance at hypothermic temperatures, such that the ratio of whole blood to preservation solution is at least about 1:0.1 by volume. In some embodiments, the volume of whole blood or preservation solution is free from an exogenously-introduced anticoagulant reagent.

As contemplated herein and described further elsewhere herein, a preferred preservation solution is protein and sera free, adapted for cellular osmotic balance of tissue, and is chemically compatible with a cryoprotectant. One preservation solution is preferably HYPOTHERMOSOL®.

BRIEF DESCRIPTION OF DRAWINGS

The present invention can be illustratively described in reference to the appended drawing in which.

DETAILED DESCRIPTION OF INVENTION

There is a need, met by embodiments of the present invention, for improved quality and extended holding times for whole blood units or components thereof. As disclosed herein, this is accomplished when such biological materials are contacted with and/or contained within an optimal nutrient-rich environment under hypothermic conditions. Furthermore, utilizing such serum-free, protein free solutions as the preferred hypothermic environment creates an optimal circumstance which allows for cryogenic preservation compatibility for cells between transport and cryoprotective solutions, in addition to eliminating xenographic biologic transmission risk. Such a preferred solution is HYPOTHERMOSOL®. Once HYPOTHERMOSOL® or a functional equivalent thereof is applied to the whole blood, a direct action of osmosis occurs which allows the cells to become fully saturated with HYPOTHERMOSOL®. This occurrence is optimal when further used in conjunction with its chemically compatible cryopreservant counterpart such as CRYOSTOR™ (BioLife Solutions, Inc., Bothell, Wash.) or a functional equivalent thereof.

The HYPOTHERMOSOL® line of preservation solutions is designed to prepare and preserve cells, tissues and organs for hypothermic (i.e., low temperature, for example, about 2-10° C.) environments and short-term hypothermic storage or transportation. For example, HYPOTHERMOSOL® has been designed to address the molecular requirements of isolated cells during a hypothermic (for example, about 2-10° C.) preservation process. It has been formulated to reduce free radical accumulation in cells undergoing hypothermic preservation, which helps mediate the level of post-storage necrosis and apoptosis thereby directly reducing the level of cell death during and following the preservation interval. For example, HTS-FRS has been demonstrated to very effective at preserving myocardial and kidney tissues, both of which have high-energy demands that can lead to free radical accumulation.

As contemplated herein, a hypothermic environment, condition or solution means an environment, condition or solution at a temperature from about 0 to about 18 degrees Celsius, preferably from about 0 to about 15 degrees Celsius, more preferably from about 2 to about 18 degrees Celsius, but more preferably from about 2 to bout 12 degrees Celsius, even more preferably from about 2 to about 10 degrees Celsius, and most preferably from about 2 to about 8 degrees Celsius.

Especially important are the benefits obtained when using the materials and methods of the present invention together with HYPOTHERMOSOL® coordinately with its specially formulated companion products from the CRYOSTOR™ family of preservation solutions when and if long-term frozen storage is so desired. Designed to prepare and preserve cells in ultra low temperature environments (for example, about −80° C. to about −196° C.), CRYOSTOR™ provides a safe, protective environment for cells and tissues during the freezing, storage, and thawing process. CRYOSTOR™, a member of BioLife's HYPOTHERMOSOL® platform, is uniquely formulated to address the molecular-biological aspects of cells during the cryopreservation process thereby directly reducing the level of Cryopreservation-Induced Delayed-Onset Cell Death and improving post-thaw cell viability and function. Through modulating the cellular biochemical response to the cryopreservation process, CRYOSTOR™ provides for enhanced cell viability and functionality while eliminating the need to include serum, proteins or high levels of cytotoxic agents. For example, CRYOSTOR™ CS-5 is a uniquely formulated cryopreservation medium containing 5% dimethyl sulfoxide (DMSO). CRYOSTOR™ has been shown to significantly improve cell viability and function following cryopreservation in comparison to traditional culture media+serum+DMSO approaches. In addition to improving overall cell survival and function, CRYOSTOR™ CS-5 also provides the advantage of being a completely defined serum- and protein-free cryopreservation medium.

It is understood that, when referenced throughout, HYPOTHERMOSOL® and CRYOSTOR™ are identified and referenced as exemplary preservation and cryopreservation solutions, respectively, and that the present invention contemplates HYPOTHERMOSOL® and CRYOSTOR™ as preferred embodiments of preservation and cryopreservation solutions, respectively, suitable for use with the blood, cells, materials and methods set forth herein. It is further understood that the present invention also contemplates functional equivalents of both HYPOTHERMOSOL® and CRYOSTOR™; all that is required is that a preservation or cryopreservation solution meet the functional requirements set forth herein and perform in a comparable manner when used in accordance with the present teachings. Functional equivalents of either HYPOTHERMOSOL® or CRYOSTOR™ can be readily identified and recognized by the skilled practitioner practicing the teachings disclosed herein.

Uses of a hypothermic preservation solution for hypothermic collection, hypothermic transport and interim hypothermic storage of whole blood products, including cellular components isolated from the same, have heretofore been undisclosed. In fact, hypothermic collection of whole blood products as described herein is contrary to conventional methodologies. That is, as described herein, whole blood is diluted significantly (at least about 1 part blood to 0.1 part preservation solution) upon collection and then transported and/or stored. Furthermore, it is contrary to conventional methodologies to collect whole blood in the absence of an anti-coagulant as described herein, as well as unexpected that specific populations of cells can still be readily isolated from such diluted preparations of whole blood using standard cell harvesting methodologies and, importantly, that such isolated cells would have at least comparable if not enhanced viability both pre- and post-preservation. These unexpected results are directly related to the optimal hypothermic environment provided by a preservation solution such as HYPOTHERMOSOL® or a functional equivalent thereof as well as the optimal cryothermic environment provided by a cryopreservation solution such as CRYSTOR™ or a functional equivalent thereof.

While utilizing CRYOSTOR™ or a like cryoprotectant which exceeds in the cryogenic process by allowing greater post thaw viability of cells with reduced concentrations of a cryoprotective agent (10% or less DMSO), thereby reducing potential toxicity, it is important to appreciate the relationship between the nutrient transport fluid HYPOTHERMOSOL® and the compatible cryopreservation media CRYOSTOR™. For example, because the nutrient solution is able to penetrate the cellular biology of cord blood components, it autonomously prepares the cells for later saturation of the selected cryopreservative required for the cryogenic process. It is significant that no washing away of the nutrient solution is necessary prior to subsequent contact with cryo-preservative. This process optimization via the elimination of any wash step to remove the nutrient matrix solution allows for greater cell viability and lessens the injury, which in turn lowers the possibility of cell damage. Additional enzymes, chemicals and/or nutrients may optimally also be added to enhance cell viability.

Although the combination of utilizing HYPOTHERMOSOL® and CRYOSTOR™ creates an optimal cryogenic freezing protocol for compatibility between the nutrient solution and cryopreservation media, other cryoprotectants can optimally be used comprising one or more agents selected from the group consisting of sucrose, trehalose, lactose, glucose, DMSO, propylene glycol, ethylene glycol, a dextran, glycerol, hydroxyethyl starch, polyvinyl pyrrolidone, formamide, 1-2-propanediol, ethanol, methanol, and polyethylene.

Currently, cord blood transplantation offers the possibility of cure for a variety of leukemias and lymphomas, multiple myeloma and other plasma cell disorders, SCID and other inherited immune system disorders, Hurler's syndrome and other inherited metabolic disorders, myelodysplastic and myeloproliferative disorders, and other malignancies including several childhood cancers.

Effective harvesting for cord blood banking necessitates that the neonate's umbilical cord be cut very early, within 30 seconds of birth (vaginal or cesarean), before it has stopped pulsing, thereby diverting the valuable blood away from the neonate. The amount of blood that cord harvesting draws is 100 mL on average (ranging from 60 mL to 180 mL) equivalent to ⅓-½ of the total blood volume of the neonate. An adequate cord blood collection requires at least 75-80 ml in order to ensure that there will be enough cells to be used for transplantation. After the collection, the cord blood unit is shipped to a lab for processing and cryopreservation.

There are two methods of cord blood collection from the umbilical vein: before the placenta is delivered (in utero), and after (ex utero). With the ex utero collection method, the cord blood is collected after the placenta is delivered and the umbilical cord is clamped off from the newborn. The established collection technique is to place the placenta in a sterile supporting structure with the umbilical cord hanging through the support. The blood is collected by gravity drainage yielding 40-150 ml of cord blood. A similar collection method is performed in utero, except that the cord blood is collected after the baby has been delivered but before the delivery of the placenta.

Once harvested, cells can be isolated from the HYPOTHERMOSOL®-whole blood suspension. Suspensions are loaded on to Ficoll-Hypaque and density centrifuged at ×435 g for 30 min. Mononuclear cells are removed carefully from the interphase layer and washed twice with HBSS plus EDTA. Total nucleated cell numbers are performed using a Coulter counter.

Alternatively, mononuclear cells are isolated from whole blood such as, for example, cord blood using PREPACYTE® (BioE; St. Paul, Minn.). By way of example, equal volumes of PREPACYTE®-WBC (BioE; St. Paul, Minn.) and umbilical cord blood are mixed in 50 mL conical tubes. Next, using a platform rocker, tubes are gently yet completely mixed (over 20 minutes at room temperature; ~15 complete rocks, back and forth per minute). Following this, the tubes are transferred to a rack, caps loosened and cells allowed to stand (without disruption or movement) for 30 minutes at room temperature for aggregation and precipitation to occur. After a clear supernatant layer and a red cell layer is observed, a transfer pipet is used to slowly and gently remove the supernatant (containing the mononuclear cells) taking care not to disturb the precipitated cells in the red cell layer. Next the supernatant is transferred to a new centrifuge tube and centrifuged at 400×g for 10 minutes. Finally the cells are resuspended in fresh medium for further processing.

It should be emphasized that once whole blood is retrieved it should be processed and used in accordance with the present invention as soon as possible in order to prevent clotting and to sustain any cells which may be present and alive. The longer an operator waits to provide the whole blood with the appropriate methods and elements as taught herein, the lower the chances of maximum recovery of viable cells.

On a related point of interest, additional stem cells from non-blood sources can be collected from the placenta via placenta cord banking. After the health care provider draws the cord blood from the umbilical cord, the placenta is couriered to the stem cell laboratory where it is processed for additional stem cells. By banking stem cells derived from the placenta as well as umbilical cord blood, families can save as much as twice the number of CD34+ stem cells for use in transplants. Having as many of these stem cells as possible is medically important: published research shows that the size of the stem cell transplant (especially the number of CD34+ cells) is consistently a significant factor in achieving a successful treatment and patient survival. In this regard, see patent application PCT/US2009/038625 entitled "Method, System and Apparatus for Hypothermic Collection, Storage, Transport and Banking of Birth Tissue, filed on even date herewith for a description of novel methods and materials specifically adapted for hypothermic collection transport and storage of various birth tissues.

In summary, it has been discovered that a hypothermic preservation solution can be used to collect whole blood and isolate cellular components therefrom as set forth herein. Any preservation solution which is formulated to reduce free radical accumulation in cells undergoing hypothermic preservation to help mediate the level of post-storage necrosis and apoptosis, thereby directly reducing the level of cell death during and following the preservation interval, is suitable for use. Moreover, further benefits are observed when long-term frozen storage of isolated cellular components is performed using a cryopreservation solution formulated to address the molecular-biological aspects of cells during the cryopreservation process thereby directly reducing the level of Cryopreservation-Induced Delayed-Onset Cell Death and improving post-thaw cell viability and function. Through modulating the cellular biochemical response to the cryopreservation process, such a cryopreservation solution can enhance cell viability and functionality while eliminating the need to include serum, proteins or high levels of cytotoxic agents.

As exemplified herein, the invention is directed to a method of harvesting whole blood, the method comprising: a) providing a volume of whole blood from a donor; and, b) mixing the volume of whole blood, or a portion thereof, with a volume of preservation solution adapted for cellular osmotic balance at hypothermic temperatures, such that the ratio of whole blood to preservation solution is at least about 1:0.1 by volume. In other preferred embodiments, the ratio of whole blood to preservation solution is at least about 1:0.5, 1:1, 1:2, 1:5, or 1:10. Preferably, the mixture of whole blood and preservation solution is maintained at about 2° C. to about 18° C. The preferred preservation solution is HYPOTHERMOSOL® (BioLife Solutions, Inc., Bothell, Wash.). In most preferred embodiments, the volume of whole blood or preservation solution is free of an exogenously-introduced anticoagulant reagent. Of significance is the unexpected discovery that hypothermic conditions can be exploited in the absence of conventional anticoagulants reagents. In certain preferred embodiments, the method further includes the step of collecting the whole blood in the presence of an anticoagulant wherein the anticoagulant is not the same as the preservation solution. In a currently preferred method, the whole blood is cord blood.

Preferably, the preservation solution contemplated herein comprises an ingredient selected from the group consisting of: an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; a biological pH buffer effective under physiological hypothermic conditions; and combinations thereof. One preferred method uses a preservation solution further comprising glutathione, a vitamin E derivative, an antioxidant, or combinations thereof.

As further exemplified herein, the invention provides a method for hypothermic storage of whole blood, the method comprising: a) diluting a volume of whole blood in a volume of preservation solution adapted for cellular osmotic balance at hypothermic temperatures, such that the ratio of whole blood to preservation solution is at least about 1:0.1 by volume; and b) maintaining the whole blood/preservation solution mixture at about 2° C. to about 18° C. The ratio of whole blood to preservation solution can be at least about 1:0.5, 1:1, 1:2, 1:5, or 1:10 and the preservation solution can be HYPOTHERMOSOL®. In certain embodiments, the whole blood is cord blood.

As additionally exemplified herein, the present invention provides a system for isolation of a component from whole blood, the method comprising: a) providing a volume of whole blood from a donor; b) mixing the volume of whole blood, or a portion thereof, with a volume of preservation solution adapted for cellular osmotic balance at hypothermic temperatures, such that the ratio of whole blood to preservation solution is at least about 1:0.1 by volume; and, c) isolating one or more components from the mixture of whole blood and preservation solution. The system can further comprise the step of: maintaining the mixture of whole blood and preservation solution at a temperature of about 2° C. to about 18° C. until the one or more components is isolated. And, the system can further comprise the step of: cryogenically freezing the one or more isolated components. The ratio of whole blood to preservation solution can be at least about 1:0.5, 1:1, 1:2, 1:5, or 1:10. The preservation solution can be HYPOTHERMOSOL®. In a preferred embodiment, the one or more components comprises stem cells, and the whole blood is cord blood.

Furthermore, the present invention is directed to a composition comprising a mixture of whole blood and a preservation solution adapted for cellular osmotic balance at hypothermic temperatures, such that the ratio of whole blood to preservation solution is at least about 1:0.1 by volume. The ratio of whole blood to preservation solution can be at least about 1:0.5, 1:1, 1:2, 1:5, or 1:10. And, the preservation solution comprises an ingredient selected from the group consisting of: an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; a biological pH buffer effective under physiological hypothermic conditions; and combinations thereof. In certain embodiments, the preservation solution further comprises glutathione, a vitamin E derivative, an antioxidant, or combinations thereof. In a preferred composition, the whole blood is cord blood.

As contemplated herein and exemplified elsewhere herein, a preferred preservation solution is protein and sera free, adapted for cellular osmotic balance of tissue, and is chemically compatible with a cryoprotectant. One preservation solution is preferably HYPOTHERMOSOL® (BioLife Solutions, Inc., Bothell, Wash.).

The invention will be further illustrated by means of the following non-limiting examples.

EXAMPLES

Methods

Preservation of Isolated Cells (Cryothermic and Hypothermic).

Cryopreservation Protocol

Suspend cell pellet directly in cold (2-8° C.) CRYOSTOR™ and transfer sample to pre-chilled cryovial. Incubate samples at 2-8° C. for 10 min, then freeze samples following standard protocol (1° C./min) either with a controlled rate freezer or Nalgene "Mr. Frosty" Isopropanol bath freezing container using a 2-step mechanical freezer protocol (2 hours at −20° C./2 hours at −80° C.), then transfer samples to liquid nitrogen for storage. Samples can be recovered by removing the sample from liquid nitrogen and immediately placing into a 37° C. water bath for 2-4 min to warm samples until just thaw (gentle agitation of the sample during the thawing interval will achieve uniform thawing of the sample). Once the sample has melted to slush phase, immediately transfer samples to a sterile environment and dilute in 37° C. culture media for cell culture.

Hypothermic Preservation Protocol

Suspend cell pellet directly in cold (2-8° C.) HYPOTHERMOSOL® and store cell suspension at 2-8° C. for 1-3 days. If cells are being plated for culture and subsequent utilization, plate cells in culture media and culture at 37° C. until cells attach. Plates can then be stored at 2-8° C. by replacing the cell culture media with HYPOTHERMOSOL® and placing plated cells into the cold for 1-3 days. Following storage, remove cells from cold, replace the HYPOTHERMOSOL® with culture media and place cells in incubation. After a recovery interval, the cells will be ready for utilization in any number of applications.

Blood Collection.

Typical aseptic venipuncture collection into either standard blood bags, or those pre-filled with volumes of HYPOTHERMOSOL® as taught elsewhere herein.

Isolation of Mononuclear Cells from Suspensions of Blood and HYPOTHERMOSOL®.

Suspensions are loaded on to Ficoll-Hypaque and density centrifuged at ×435 g for 30 min. Mononuclear cells are removed carefully from the interphase layer and washed twice with HBSS plus EDTA. Total nucleated cell numbers were performed using a Coulter counter.

Alternatively, mononuclear cells are isolated from cord blood using PREPACYTE®. For this, equal volumes of PREPACYTE®-WBC and umbilical cord blood are mixed in 50 mL conical tubes. Next, using a platform rocker, tubes are gently yet completely mixed (over 20 minutes at room temperature; ~15 complete rocks, back and forth per minute). Following this, the tubes are transferred to a rack, caps loosened and cells allowed to stand (without disruption or movement) for 30 minutes at room temperature for aggregation and precipitation to occur. After a clear supernatant layer and a red cell layer is observed, a transfer pipet is used to slowly and gently remove the supernatant (containing the mononuclear cells) taking care not to disturb the precipitated cells in the red cell layer. Next the supernatant is transferred to a new centrifuge tube and centrifuged at 400×g for 10 minutes. Finally the cells are resuspended in fresh medium for further processing.

For culture of mononucleated cells, cell pellets are resuspended with 20 ml standard culture-cell culture medium and plated in a T-75 flask. The cell culture medium used is a mixture of 60% Dulbecco's Modified Eagle Medium and 40% MCDB 105 medium supplemented with 10% FCS and 1% Penicillin-Streptomycin.

Flow Cytometry

Total Nucleated Cell Count.

A total nucleated cell count (TNC) represents all the nucleated cells including nucleated red blood cells. The total nucleated cell (TNC) along with $CD34^+$ cell dose has been shown to be a crucial determinant of hematopoietic recovery and overall outcome following UCBT, and the limited cell dose of single UCB units is clearly the most important barrier to its more widespread use, especially in adults. The TNC is typically obtained by use of a coulter counter but the number can be obtained by a variety of measures.

Multi-Plex Protocol for TNC, Viability (7-AAD), CD34, and CD45.

Mononuclear cells may be quantitated by subtype in blood samples using immunofluorescent methods and flow cytometry. Antibodies are used to quantify and purify hematopoietic progenitor stem cells for research and for clinical bone marrow transplantation. Cells observed as CD34$^+$ are of an undifferentiated form, primitive form and are considered pluripotent hematopoietic stem cells.

In order to determine viability and nucleated cell counts, including CD34 and CD45 subpopulations, obtain a 12×75 mm tube and transfer 2 ml of ammonium hemolytic buffer solution to the tube. Next, if not already done, perform a cell count on the specimen to determine the volume needed. Add the calculated volume of sample to the tube and vortex to allow for lysis of red blood cells. Once lysed, spin the tube in the centrifuge at 1500 rpm for 2 minutes. Decant the supernatant and wash with 2 ml of wash solution. Centrifuge sample and perform wash again. Following wash, remove supernatant and add 7-AAD (eBioscience, catalog number 00-6993-50), CD34 (Becton Dickenson, catalog number 340669), and CD45 staining antibodies (Becton Dickenson, catalog number 340664). Resuspend pellet in staining solution and place tube/sample at 4 C for 20-30 minutes. Following the incubation, add wash solution and centrifuge. Decant the supernatant, add flow solution and perform flow cytometry.

CFU Assay.

The colony forming unit assay is a cytologic technique for measuring the functional capacity of stem cells by assaying their activity. The assay is essentially an assessment of individual cells and the ability to clone themselves into an entire colony of identical cells.

Once the mononuclear cells are separated and collected, perform a cell count and record the total number prior to cryopreservation. Using the total number, two separate cell concentrations should be (typically $3\times10^4$/ml and $1\times10^5$/ml) prepared in methylcellulose. Note, the cells should be plated in a volume of 1 ml per each of 4 plates at a ratio of 1:10 (v:v) cells to methylcellulose. Due to the viscosity of the methylcellulose, a total volume of 5 ml (cells, methylcellulose, and media) must be prepared in order to plate 4-1 ml plates. From the cell count of the specimen, multiply each of the desired cell concentrations by 5 to determine the total number of cells needed. Add the appropriate number of cells and media (IMDM) to the methylcellulose bringing the total volume to 5 ml and mix the contents. Dispense 1 ml of the suspension to each of 4-10×35 mm tissue culture dishes. Gently swirl to rotate the contents of each plate so that the entire bottom of the plate is evenly covered. Place the plates into a larger Petri dish along with a hydration plate containing sterile distilled water. Place cultures in a 37° C., 5% $CO_2$ incubator and store for 14 days. Following the incubation, the colonies will be counted. The types of colonies counted are: Burst Forming Unit-Erythrocyte (BFU-e), Colony Forming Unit (CFU), and sometimes Colony Forming Mixed (CFU-Mix). Once counted, calculations are performed based upon the starting number of cells to determine the total number of each colony-type for a product. If cells are being prepared for cryopreservation, colony assays can be set up in a similar fashion from post-thaw cultures to determine the number of colonies and efficacy of the preservation process.

Viability Assays

ALAMAR BLUE™

ALAMAR BLUE™ is soluble, stable in culture medium and is non-toxic. The continuous monitoring of cells in culture is therefore permitted. Specifically, ALAMAR BLUE™ does not alter the viability of cells cultured for various times as monitored by Trypan Blue exclusion. Cells grown in the presence of ALAMAR BLUE™ and subsequently analyzed by Flow Cytometry for CD44, CD45RB, CD4 and heat stable antigen are found to produce similar numbers of viable cells and antigen expressing cells as non-ALAMAR BLUE™ exposed cells. Because ALAMAR BLUE™ is non-toxic, the cells under study can be returned to culture or used for other purposes including histological studies. Proliferation measurements with ALAMAR BLUE™ may be made either spectrophotometrically by monitoring the absorption of ALAMAR BLUE™ supplemented cell culture media at two wavelengths. Alternatively, proliferation measurements with ALAMAR BLUE™ may be made fluorometrically.

Calcein-AM

The Calcein-AM assay provides a simple, rapid and accurate method to measure cell viability and/or cytotoxicity. Calcein-AM is a non-fluorescent, hydrophobic compound that easily permeates intact, live cells. The hydrolysis of Calcein-AM by intracellular esterases produces calcein, a hydrophilic, strongly fluorescent compound that is well retained in the cell cytoplasm. Cells grown in plates can be stained and quantified in less than two hours.

Assessment immediately post-thaw tends to render incomplete and inaccurate data regarding sample viability and function; therefore, it is recommended that viability assessment be performed 24 to 48 hours post-thaw. Viability and yield assessment immediately following thawing may be helpful in evaluating the extent of delayed onset cell death (i.e. when comparing 1-hour post-thaw values to 24-hours post-thaw values); however, when determining preservation efficacy, make sure assessment is performed with careful attention and comparison of both yields and viability between pre-freeze values, post-thaw values, and 24-48 hrs post-thaw. This will allow for an accurate determination of sample status and preservation efficacy.

Example 1

Hypothermic Whole Blood Collection

Umbilical cord blood collection (without cord tissue). After delivery of the neonate, cross-clamp and cut the umbilical cord, then follow one of two approaches:

Closed System Method

After delivery of the placenta, the proximal and distal ends of the umbilical cord are swabbed with alcohol, allowed to dry and swabbed again with iodine tincture. A 16 G needle attached to a blood collection bag containing a volume of HYPOTHERMOSOL® is inserted into the proximal site as close to the clamp as possible. Blood will begin to fill the bag via gravity drainage. The distal end is then immediately cannulated with a 16 G angio-cath. A 50 ml syringe pre-filled with HYPOTHERMOSOL® is attached to the cannula via luer-lock, and the blood is flushed from the umbilical cord into the collection bag. A total of 150 ml of solution (3 syringes) should be used to completely flush the blood into the collection bag. After collection, the bag is sealed by tying three knots in the tubing of the collection line, leaving at least 6 inches of exposed tubing between the knots and the bag.

Alternate Collection Method

The proximal end of the umbilical cord can either be submerged in a 250 ml collection container containing 50 ml HYPOTHERMOSOL® plus anticoagulant then unclamped, or a 16 G needle attached to a 250 ml blood collection bag as described in the closed-system method can be used. The blood is then "milked" by applying pressure to the cord between the thumb and hooked forefinger and gently pulling in a distal-proximal direction. This process can be repeated until the desirable volume of blood is collected.

Example 2

Blood Cells Stored in Hypothermic Conditions Retain Viability Post-Sedimentation Umbilical cord blood was collected at donor sites by venipuncture into citrate-phosphate-dextrose containing blood bags (Baxter US Healthcare). After determination that the unit is "research grade" (TNC≤9×10$^8$) the unit was split evenly into two transfer bags. Cold (2-8° C.) HYPOTHERMOSOL® was added to one bag at a 1:1 ratio with the blood volume and stored at 4° C. The other half of the unit served as control and was held at room temperature. Samples were processed after 24 hours and viable total nucleated cell count recoveries were determined via flow cytometry after sedimentation and again after plasma reduction. Controls were held a room temperature for the same duration. Results were expressed as percent recovery as compared to the total nucleated cell count recoveries of the initial blood draw at the time of collection.

To determine if HTS-FRS+Hetastarch can act as a gravity sedimentation solution in order to streamline cord blood processing and improve recovery and viability of TNCs, three cord blood units were each split in half and processed with the following solutions: 1) Standard Sedimentation Solution: Hetastarch (40%), 0.9% NaCl (48%), 6% ACD-A (12%); 2) HTS-FRS (60%), Hetastarch (40%). After 1 hour, the blood containing Standard Sedimentation Solution had sedimented completely; however, the blood containing HTS-FRS Sedimentation Solution required 90 minutes to sediment. Blood diluted 1:1 with HTS-FRS and stored at 4° C. demonstrated recoveries of 74.52% post-sedimentation and 72.12% post-plasma reduction as compared to recoveries of 90.98% post-sedimentation and 93.98% post-plasma reduction from non-diluted samples stored at room-temperature, evidencing that blood cells stored in HYPOTHERMOSOL® retain their viability after sedimentation and further processing.

Example 3

Figure 1:
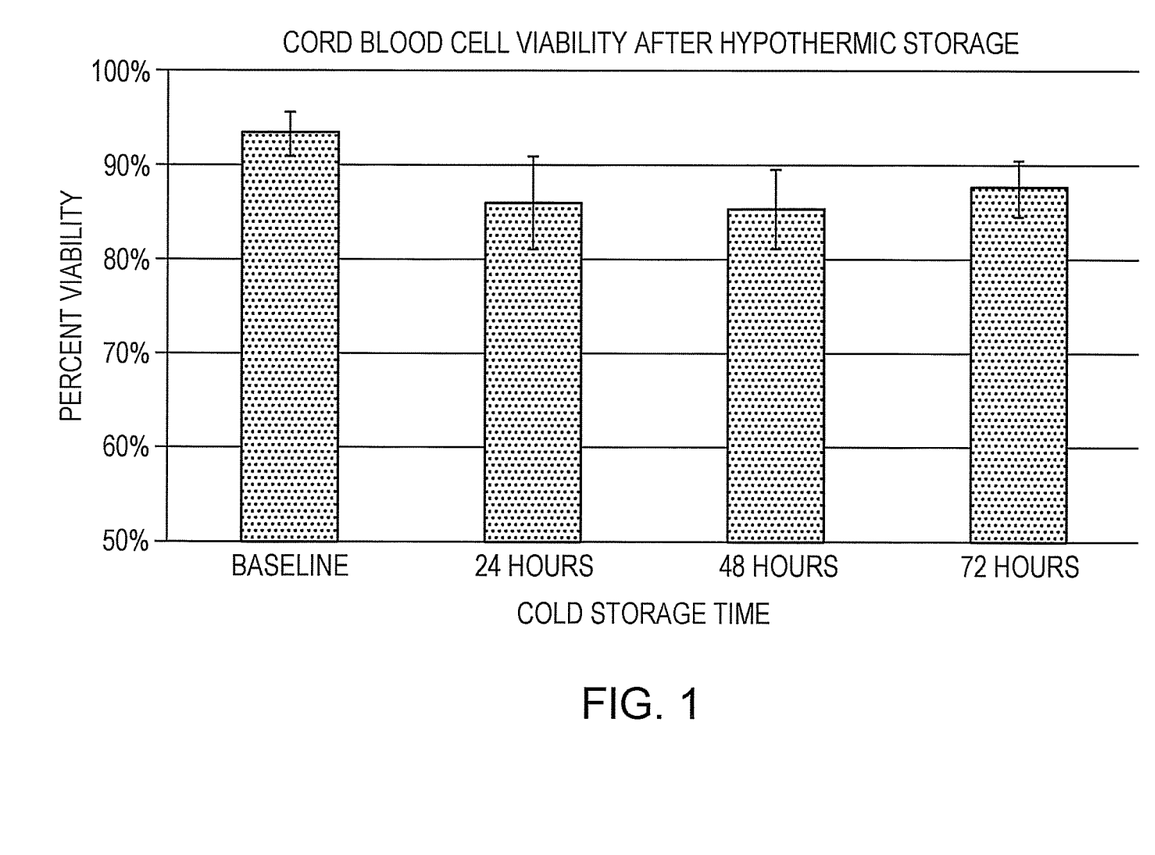
FIG. 1 is a bar graph showing blood cell viability after hypothermic storage in HYPOTHERMOSOL®, in accordance with an illustrative embodiment of the invention.

Blood Cells Stored in Hypothermic Conditions for Extended Periods Retain Viability Umbilical cord blood was collected at the time of surgery at donor sites from 3 scheduled C-sections by venipuncture into collection bags (Pall Medical) that had been pre-filled with 35 ml of cold (4° C.) HYPOTHERMOSOL®. No anti-coagulant was added. Collection volumes were 87.3, 72, and 85 ml. The units were stored for up to 72 hours at 4° C. and were monitored every 24 hours for coagulation by visual determination of clot formation. TNC viability was determined at each time point using 7-AAD and flow cytometry. No clotting was observed at any time point and, as shown in FIG. 1, cell viabilities were maintained over 72 hours of cold storage as compared to baseline (initial blood draw at the time of collection). In FIG. 1, error bars are +/−1 standard error of the mean. These data demonstrate that cell viability is retained during extended periods of hypothermic storage of whole blood in HYPOTHERMOSOL®. Moreover, these data validate the use of HYPOTHERMOSOL® to store whole blood for extended periods in the absence of anticoagulants.

Example 4

Figure 2:
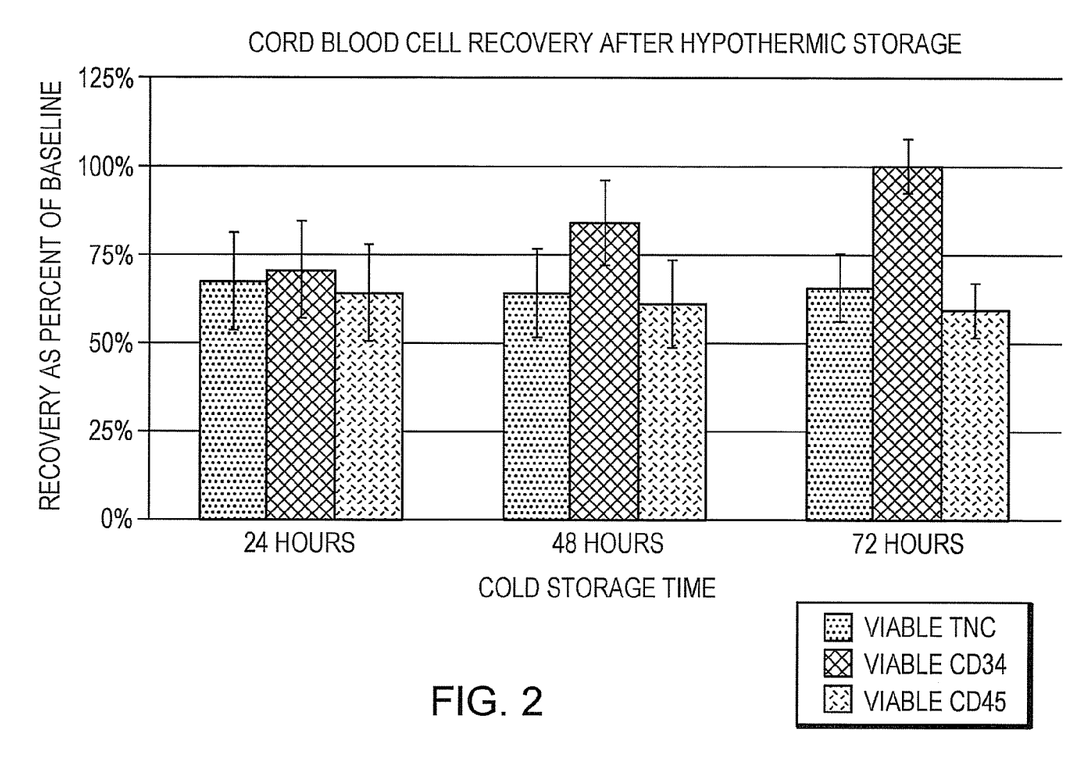
FIG. 2 is a bar graph showing recovery of viable nucleated cells, and CD34 and CD45 positive cells, in accordance with an illustrative embodiment of the invention.

Significant Cell Types were Preserved and Recoverable when Collected and Stored in Hypothermic Conditions Cord blood from three donors was collected as described in Example 3. No anti-coagulant was added. After 24, 48 and 72 hrs storage at 4° C. in HYPOTHERMOSOL®, a 25 ml sample of the cord blood was removed for processing; a 1 ml aliquot was taken for pre-processing testing and the remaining 24 ml was processed using standard cord blood processing methods. Flow cytometry was utilized to determine pre-processing yield, TNC recovery, viability using 7-AAD, and CD34 and CD45 positivity. As shown in FIG. 2, compared to baseline (initial blood draw at the time of collection), viable TNC, CD34$^+$, and CD45$^+$ cell counts decreased slightly within the first 24 hours, but stabilized for the remainder of the 72 hour cold storage. In FIG. 2, error bars are +/−1 standard error of the mean.

Figure 3:
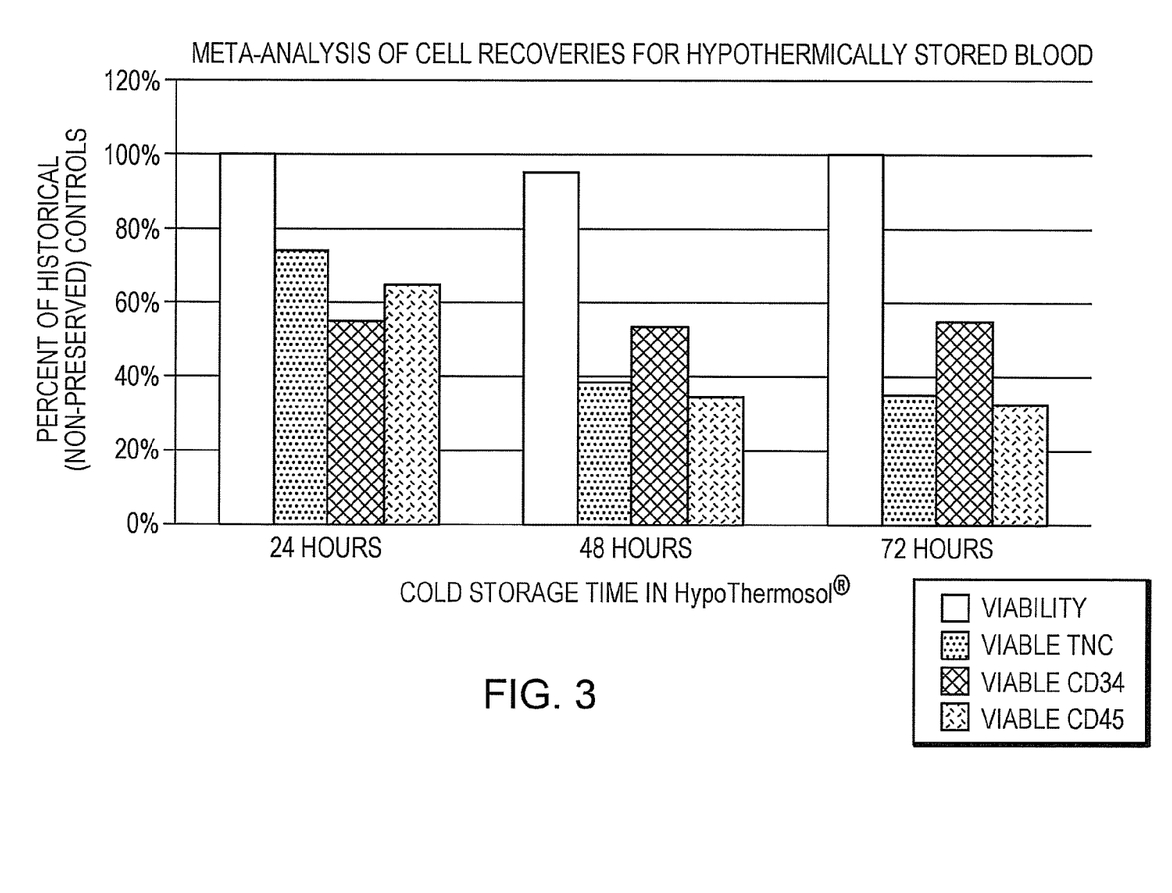
FIG. 3 is a bar graph comparing average viability from blood samples collected into bags pre-filled with HYPOTHERMOSOL® as compared to average values from blood samples collected in bags containing anticoagulant, in accordance with an illustrative embodiment of the invention.

After depletion of the RBCs and plasma the Total Nucleated Cell population was re-suspended in 10 ml of IMDM for post-processing testing. Flow cytometry was utilized to determine post-processing yield, TNC recovery, viability using 7-AAD, and CD34 and CD45 positivity. Data is compared to 8 randomly selected non-preserved cord blood samples collected using venipuncture collection in standard citrate-phosphate-dextrose collection bags (Baxter) in the absence of HYPOTHERMOSOL®. FIG. 3 shows average viability, viable TNC, viable CD34$^+$, and viable CD45$^+$ from three cord blood units collected into bags pre-filled with HYPOTHERMOSOL® without anticoagulant and stored at 4° C. for 24, 48, or 72 hours. As shown in FIG. 3, cell viability is maintained for 72 hours. Viable TNC, CD34$^+$, and CD45$^+$ cell counts decreased slightly within the first 24 hours, but stabilized for the remainder of the 72 hour cold storage. These data demonstrate that relevant cell types (e.g., stem cells) are viable and recoverable after extended periods of hypothermic storage of whole blood in HYPOTHERMOSOL®. Moreover, these data validate the use of HYPOTHERMOSOL® to store whole blood for extended periods in the absence of anticoagulants.

In FIGS. 1, 2 and 3, viable TNC, viable CD34$^+$, and viable CD45$^+$ were calculated as follows:

Viable TNC=(% viability)×(NC/ml)×(volume)

Viable CD34$^+$=(% CD34$^+$ in NC count)×(viable TNC)

Viable CD45$^+$=(% CD45$^+$ in NC count)×(viable TNC).

Example 5

Hypothermic Storage of Whole Peripheral Blood in Hypothermic Conditions

Peripheral blood will be drawn according to standard techniques with and without acid-citrate-dextrose anticoagulant. From the initial sample, 40M cells will be dispensed into each of 5 tubes and diluted 1:0.1, 1:0.5, 1:1, 1:2, 1:5, and 1:10 with volumes of HYPOTHERMOSOL® (2-8° C.). Negative control vials will be undiluted blood at room temperature and undiluted blood at 4 C. Samples will be assayed at 18, 36, and 72 hours by flow cytometry for total nucleated cell count, viability, and CD34 and CD45 positivity. A sample of the initial blood draw will be assayed immediately after donation to serve as a baseline control.

It is expected that cells from whole peripheral blood, when collected, isolated and stored in the presence of HYPOTHERMOSOL® or an equivalent thereof at hypothermic conditions, will show at least comparable viability and recoverability over time at hypothermic conditions as compared with conventionally processed cells. Thus this study will demonstrate that, once again, the benefits of the present invention exemplified above in Examples 1-4 will also be applicable to peripheral whole blood and cells obtained therefrom.

Based on the foregoing teachings, it is now evident that whole blood collected and stored using the materials and methods disclosed herein, has improved integrity and its BC content has improved viability and recoverability when compared with currently available standard methods of collection and storage. And, it is now evident that stem cells isolated from such whole blood exhibit high viability and rates of recovery compared to standard preparations. In addition, it is expected that cell viability and recovery will be maintained beyond 72 hours, preferably for up to least 7 days, 14 days, 21 days, or longer when collected, processed, and/or stored under the conditions and in accordance with the practices described herein.

Based on the discoveries described and illustrated herein, heretofore undescribed compositions and methods result in unexpected viability and integrity of whole blood collected in hypothermic conditions when compared to conventionally collected whole blood. And further, whole blood components obtained in accordance with the present invention exhibit less structural, chemical and/or functional damage as compared to conventionally isolated components. Even further, it is expected that such isolated components, when subsequently cryopreserved in accordance with the teachings set forth herein, will recover to a greater extent and exhibit greater viability and functionality as compared to conventionally collected whole blood. The teachings of the present invention are particularly effective for cord blood collection and cells isolated therefrom, especially stem cells.

EQUIVALENTS

The invention may be embodied in other specific forms without departing from the spirit or essential characteristics thereof. The present embodiments are therefore to be considered illustrative and not restrictive, the scope of the invention being indicated by the appended claims rather than by the foregoing description, and all changes that come within the meaning and range of equivalency of the claims are therefore intended to be embraced therein.

We claim:

1. A method of harvesting whole blood, the method comprising:
    a) providing a volume of whole blood from a donor; and,
    b) mixing, in a container, the volume of whole blood, or a portion thereof, with a volume of preservation solution adapted for cellular osmotic balance at hypothermic temperatures, such that the ratio of whole blood to preservation solution is at least about 1:0.1 by volume,
    c) maintaining the mixture of whole blood and preservation solution at hypothermic temperatures,
    wherein the volume of whole blood, the volume of preservation solution, and the container are free from an exogenously-introduced anticoagulant reagent, and
    wherein the preservation solution comprises an ingredient selected from the group consisting of: an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; a biological pH buffer effective under physiological hypothermic conditions; and combinations thereof.

2. The method of claim 1, wherein the ratio of whole blood to preservation solution is at least about 1:0.5, 1:1, 1:2, 1:5, or 1:10.

3. The method of claim 1, wherein the mixture of whole blood and preservation solution is maintained at about 2° C. to about 18° C.

4. The method of claim 1 wherein the preservation solution comprises an aqueous solution of electrolytes containing potassium ions at a concentration range of from about 35 to about 45 mM, sodium ions at a concentration range of from about 80 to about 120 mM, magnesium ions at a concentration range of from about 2 to about 10 mM, chloride ions at a concentration range of from about 15 to about 20 mM, and calcium ions at a concentration range of from about 0.01 to about 0.1 mM; an impermeant anion; mannitol; a macromolecular oncotic agent; at least one simple sugar; a substrate for the regeneration of ATP; and a biological pH buffer effective under physiological hypothermic conditions.

5. The method of claim 4 wherein the preservation solution further comprises glutathione, a vitamin E derivative, an antioxidant, and combinations thereof.

6. The method of claim 1 wherein the whole blood is cord blood.

7. The method of claim 1, wherein the mixture of whole blood and preservation solution is maintained at about 2° C. to about 18° C. for at least 24 hours.

8. The method of claim 1, wherein the mixture of whole blood and preservation solution is maintained at about 2° C. to about 18° C. for at least 48 hours.

9. The method of claim 1, wherein the mixture of whole blood and preservation solution is maintained at about 2° C. to about 18° C. for at least 72 hours.

10. The method of claim 1, wherein the mixture of whole blood and preservation solution is maintained at about 2° C. to about 18° C. for at least 7 days.

11. The method of claim 1, wherein the mixture of whole blood and preservation solution is maintained at about 2° C. to about 18° C. for at least 14 days.

12. The method of claim 1, wherein the mixture of whole blood and preservation solution is maintained at about 2° C. to about 18° C. for at least 21 days.

* * * * *